United States Patent [19]

Takahashi et al.

[11] Patent Number: 4,577,338
[45] Date of Patent: Mar. 18, 1986

[54] X-RAY FLUORESCENCE SPECTROMETER AND METHOD OF CALIBRATING THE SAME

[75] Inventors: Yoshihiro Takahashi; Maria A. Rey, both of San Jose, Calif.

[73] Assignee: Xertex Corporation, Santa Clara, Calif.

[21] Appl. No.: 438,008

[22] Filed: Nov. 1, 1982

[51] Int. Cl.⁴ ............................................ G01N 23/223
[52] U.S. Cl. ...................... 378/048; 378/44; 378/207
[58] Field of Search ............. 378/48, 45, 207, 46, 378/86, 44

[56] References Cited

U.S. PATENT DOCUMENTS

| | | | |
|---|---|---|---|
| 3,198,944 | 8/1965 | Furbee | 378/48 |
| 4,015,124 | 3/1977 | Page | 378/45 |
| 4,037,099 | 7/1977 | Oda et al. | 378/86 |
| 4,150,288 | 4/1979 | Inoue et al. | 378/207 |

FOREIGN PATENT DOCUMENTS

54-59193  5/1979  Japan ...................... 378/45

Primary Examiner—Alfred E. Smith
Assistant Examiner—T. N. Grigsby
Attorney, Agent, or Firm—Flehr, Hohbach, Test, Albritton & Herbert

[57] ABSTRACT

X-ray fluorescence spectrometer for determining the sulfur content of oil and other matrices, and method of calibrating the same. The spectrometer comprises a pulse height analyzer and a computer for analyzing the energy spectrum of photons emitted by a sample in regions corresponding to the energy levels of photons emitted by sulfur and the target line x-rays scattered by the sample. The windows through which the energy is sampled are adjusted to provide a calibration curve of predetermined shape, and a built-in standard is analyzed and a value corresponding to the ratio of the relative intensities of the fluorescent energy from the standard and the scattered target line x-ray radiation is stored during initial calibration of the system. Thereafter, the system is recalibrated simply by analyzing the build-in standard again, adjusting the sampling windows, and adjusting a constant in the relationship by which the sulfur content is determined to compensate for drift in the system.

20 Claims, 7 Drawing Figures

FIG_1

FIG_2

FIG_3

FIG_4

FIG_5     FIG_6

FIG_7

X-RAY FLUORESCENCE SPECTROMETER AND METHOD OF CALIBRATING THE SAME

This invention pertains generally to x-ray fluorescence spectroscopy, and more particularly to an x-ray fluorescence spectrometer for determining the sulfur content of oil and other matrices and to a method of calibrating the same.

In the petroleum industries, the determination of sulfur content in crude oils and other hydrocarbons is important because sulfur is known to poison catalysts used in various stages of oil refining processes.

The majority of sulfur measurements are made by x-ray fluorescence spectroscopy, which provides certain advantages over other techniques, such as speed of analysis, ease of operation, and the nondestructive nature of the measurement.

However, the x-ray fluorescence technique also has certain limitations and disadvantages, one of which being that the fluorescent intensity from sulfur is dependent upon the composition of a sample as well as the concentration of sulfur. Thus, for example, the response from a 1.0% sulfur concentration in benzene is not the same as from a similar concentration in hexane. This phenomenon is known as the matrix effect.

One approach heretofore employed to solve this problem is to prepare a daily calibration curve with standards of the same matrix as the sample to be analyzed. If another sample in a different matrix is to be analyzed, it is necessary to prepare another calibration curve with standards in that matrix. This approach is cumbersome and time consuming. Furthermore, sometimes the matrix of a sample is unknown, making it impossible to prepare a reliable calibration curve.

Numerous other methods have also been proposed to overcome the matrix effects. Many of these approaches are based on mathematical models and typically deal with a wide variety of matrices. Some models do not require any calibration standards, but involve complex calculations and massive amounts of data to make the matrix corrections.

Another method of correcting for matrix effects is based on a semitheoretical or empirical approach. Even though the applicability of this approach may be somewhat limited, it is in some ways more practical than mathematical models, particularly when x-ray tube excitation is employed. With such excitation, the incident x-ray contains the Bremsstrahlung continuum as well as the characteristic target line radiation, and the mathematical treatment of the continuum becomes uncertain. The empirical approach can also compensate for nonideal situations which mathematical models might not be able to predict. Another advantage of the empirical approach is that it does not involve the solution of complex equations and does not require a large computer.

Scattered x-ray intensity has been used successfully for correcting the matrix effect in certain applications. The emitted sulfur line from a specimen is absorbed by the specimen before it reaches the detector. At the same time, the scattered line is also absorbed by the specimen. The absorption is proportional to the overall mass-absorption coefficient of the specimen at any given wavelength. The scattered line for the matrix correction can be selected at the background adjacent to the sulfur line or the scattered x-ray tube target line.

One disadvantage of this approach is that it requires repeated calibration with at least two or three standards of known sulfur content. In the case of sulfur in oil, the relationship between the sulfur line intensity and the sulfur content of the sample is nonlinear. The preparation of the calibration curve is further complicated because the components in an x-ray fluorescence spectrometer are subjected to drift and are not stable enough to maintain the calibration curve for a long period of time. Consequently, such systems must be recalibrated frequently, typically as much as two or more times a day, and each recalibration requires the use of at least two or three standards. The problem is further complicated if the sulfur concentration of the standard should change, e.g. due to volatilization.

It is in general an object of the invention to provide a new and improved x-ray fluorescence spectrometer and method of calibrating the same which overcome the foregoing and other problems heretofore encountered with such spectrometers.

Another object of the invention is to provide a spectrometer and method of the above character which provide accurate and reliable results with a minimum of calibration time.

These and other objects are achieved in accordance with the invention by providing a spectrometer comprising a pulse height analyzer and a computer for analyzing the energy spectrum of x-ray photons emitted by the sample in regions corresponding to the energy levels of photons emitted by sulfur and target line x-rays scattered by the sample. The windows through which the energy is sampled are adjusted to provide a calibration curve of predetermined shape. A single sulfur standard is analyzed, and information from its spectrum is stored during the initial calibration of the system. Thereafter, the system is recalibrated simply by analyzing the sulfur standard again, readjusting the sampling windows to maintain a consistent conversion, and adjusting a constant in the relationship by which the sulfur content is determined to compensate for drift in the system. The scattered target line x-rays are utilized to compensate for the matrix effects.

Figure 1:
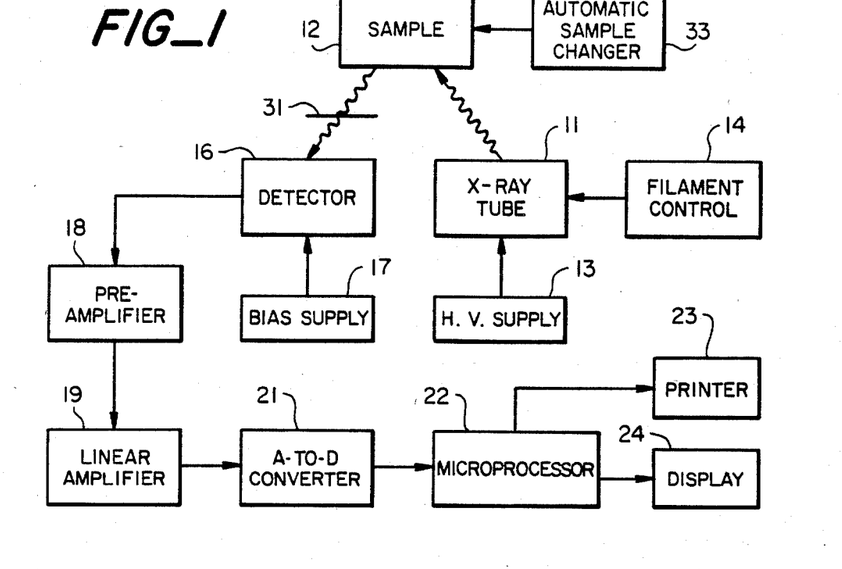
FIG. 1 is a block diagram of one embodiment of an x-ray fluorescence spectrometer according to the invention.

As illustrated in FIG. 1, the spectrometer comprises an x-ray source 11 for irradiating a sample 12 with a beam of x-rays. For measuring sulfur contents in oil, an x-ray tube with a titanium target is a suitable primary x-ray source. However, any other suitable source of x-rays can be employed. The x-ray tube is energized by a high voltage supply 13 and a filament control 14.

When the primary x-ray beam generated by an x-ray tube is irradiated on a sample, two things can occur. When the beam is absorbed and the primary x-ray has a higher energy than the bonding energy of K-shell electrons of the elements in the sample, K-shell electrons are ejected. This vacancy is then immediately filled by an electron from an outer shell, and to restore the energy balance, the atom emits a photon. The photon has an energy specific to the element, and its intensity is related to the concentration of the element in the sample. If the primary x-ray beam is not absorbed, it is scattered, and the intensity of the scattered x-rays is related to the elements in the sample or matrix.

X-ray photons emitted by the excited specimen are detected by a detector 16 which produces electrical signals corresponding to the energy at different levels within the spectrum. Suitable detectors include a lithium drifted silicon detector and a gas filled proportional counter. A biasing current is applied to the detector by a bias supply 17. Signals from the detector are supplied to a preamplifier 18, and the output of the preamplifier is connected to the input of a linear amplifier 19. The signal at the output of amplifier 19 is an analog signal which varies in amplitude in accordance with the fluorescent energy produced by the excited sample.

The output of amplifier 19 is connected to the input of an analog-to-digital converter 21 which serves as a pulse height analyzer. The output of this converter is applied to a microprocessor 22 having a printer 23 and a display 24 associated therewith.

Figure 2:
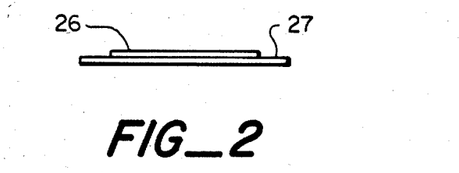
FIG. 2 is a side elevational view of one embodiment of a sulfur standard for use in the spectrometer of FIG. 1.

As discussed more fully hereinafter, a built-in solid standard is utilized in the calibration of the spectrometer. It has been found that polysulfone film, a sulfur containing polymer, is a stable and convenient standard for this purpose. FIG. 2 illustrates an example of a solid sulfur standard having two layers of film 26, 27 laminated together to form a body of suitable overall, or apparent, sulfur content. The overall or apparent sulfur content is determined by the sulfur contents and the relative thicknesses of the laminates and can be adjusted as desired by suitable selection of these parameters. For example, a 6 mil layer of a polymer film such as polysulfone containing about 5% sulfur laminated with a 4 mil layer of a non-sulfur containing film such as polyethylene provides an overall or apparent sulfur content of about 1%. The photons emitted by sulfur atoms in the polysulfone film are attenuated when they penetrate the polyethylene film, resulting in an apparent sulfur content which is lower than the sulfur content of the polysulfone. In the presently preferred embodiment, the sulfur standard is built into the spectrometer and constitutes an integral part thereof. However, an external standard and/or a liquid standard can also be employed, although a liquid standard may not be as stable as a solid one.

Since sulfur is the element of interest, a sulfur containing solid standard is preferred. However, the primary function of the standard is to provide the information on the electronic drift, and other elements having characteristic fluorescence x-ray lines falling between about 1.0 KeV and 4.0 KeV can be used. With such elements, the same amount of electronic drift correction is applicable to both sulfur and the element in the standard. Examples of such elements are lead, molybdenum, chlorine and phosphorous.

Figure 3:
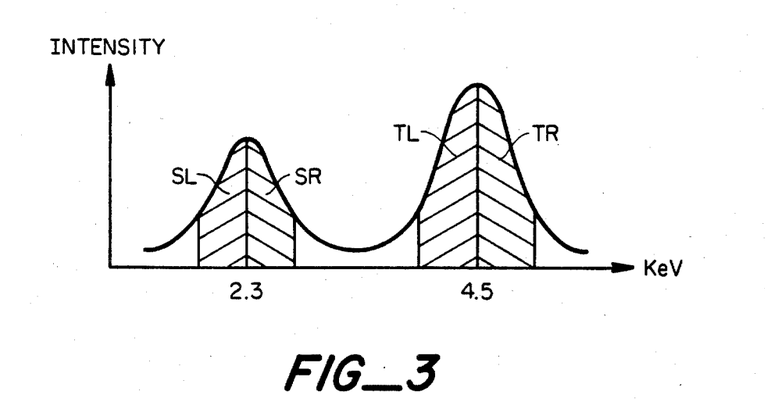
FIG. 3 is a graphical representation of an x-ray spectrum obtained with the spectrometer of FIG. 1.

FIG. 3 illustrates the x-ray spectrum of a sample of crude oil excited with x-rays from a titanium target with a characteristic x-ray energy of 4.5 KeV. The major elements of oil are carbon and hydrogen which have relatively low fluorescence yields and x-ray energies which are generally too low to be detected. Therefore, only x-ray fluorescence from sulfur in the oil sample is detected, and the characteristic x-ray energy of this element is 2.3 KeV. Thus, a typical x-ray spectrum for crude oil excited with x-rays from a titanium target x-ray tube has a sulfur fluorescence peak at 2.3 KeV and a titanium scattered x-ray peak at 4.5 KeV.

A filter 31 is positioned between the sample and the detector to prevent interference from other elements which may be present either in the specimen itself or in the specimen chamber. For example, a specimen of oil might have one or more chlorine containing additives, and argon may be present in the form of air in the specimen chamber. Both of these elements have energy peaks near the sulfur peak and could interfere with the determination of the sulfur content. Suitable filter materials for use in detecting sulfur include pure sulfur and molybdenum, and one presently preferred filter comprises a polymer film containing sulfur.

Samples to be analyzed are carried by an automatic sample changer 33, together with the built-in standard. The changer includes a carrier which holds the standard and a plurality of samples for selective exposure to the x-rays from source 11.

Microprocessor 22 is programmed to calculate the sulfur content of the sample from the intensities of the sulfur line and the scattered line in the fluorescence spectrum. It has been determined empirically that the sulfur content in various oils and hydrocarbon matrices can be determined to a high degree of accuracy with a single calibration curve based upon the following relationship $$S = a(kX)^2 + b(kX) + c,$$

where S is the sulfur content in percent; a, b and c are constants, and $X = SR/TR + SL/TL$. As illustrated in FIG. 3, SL and SR are areas under the spectral curve on either side of the sulfur fluorescence peak, and TL and TR are areas under the curve on either side of the scattered x-ray peak. Other relationships which utilize the scattered radiation to correct the matrix effects can be utilized, if desired. For example, the entire sulfur peak can simply be divided by the scattered peak $$\left( X = \frac{SL + SR}{TL + TR} \right).$$

However, the separation of the peaks into left and right halves is preferred in that it provides additional information for correcting the electronic drift as well as correcting the matrix effects.

It has been found that if SL, SR, TL and TR are exactly matched to the defined areas under the sulfur fluorescence peak and the scattered x-ray peak, the constants a, b and c remain the same for one particular instrument. In other words, the shape of the calibration curve is fixed for each instrument within a particular calibration range. This matching is done by adjusting the windows through which energy in the regions of SL, SR, TL and TR is sampled.

Figure 4:
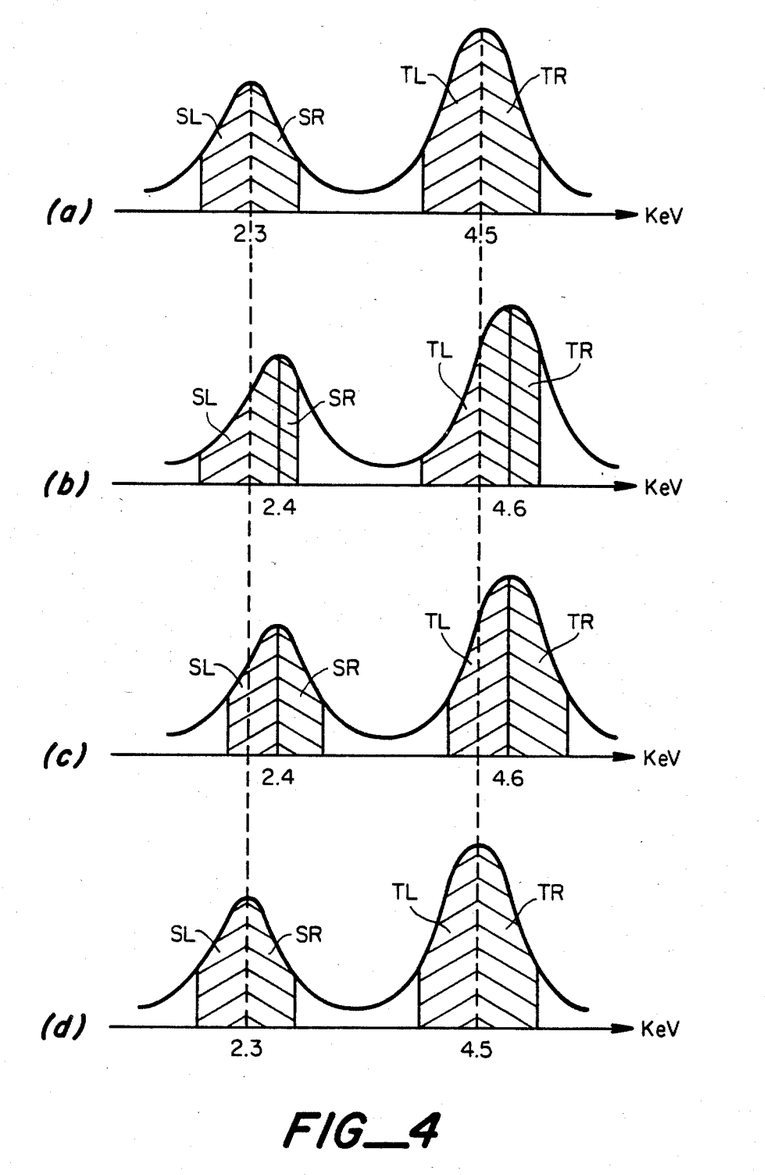
FIG. 4 is a graphical representation similar to FIG. 3 showing the effect of drift and its compensation in the embodiment of FIG. 1.

Initially, SL, SR, TL and TR are adjusted to be centered precisely about the sulfur and scattered titanium lines as shown in FIGS. 3 and 4(a). Thereafter, however, the spectrum may appear to shift due to instability of components in the spectrometer. In the embodiment illustrated in FIG. 1, the principal sources of instability or drift are detector 16, bias supply 17, x-ray tube power supply 13, and linear amplifier 19. Some change in the Bremsstrahlung continuum may occur as the x-ray tube ages, and the filament control 14 for the x-ray tube can also cause some drift. This drift, however, is relatively unimportant due to the ratioing technique employed in the invention. Additional drift can also occur in the zero level of the analog-to-digital converter 21 and in the preamplifier 18.

As a result of the drift or instability in the spectrometer, the windows which provide areas SL, SR, TL and TR may no longer be aligned with the sulfur line and the scattered x-ray line. A somewhat exaggerated example of such drift is shown in FIG. 4(b). In this example, the sulfur peak appears to occur at 2.4 KeV, and the titanium peak appears to occur at 4.6 KeV, while the windows appear to be centered at the actual energy level of the peaks. Compensation for this apparent shifting of the spectrum can be provided either by shifting the windows to the apparent peaks, as illustrated in FIG. 4(c), or by moving the peaks back to their proper positions, as illustrated in FIG. 4(d). In either case, the sulfur content can still be accurately determined after the correction has been made.

Calibration of the spectrometer is done in two phases: (1) an initial calibration in which the system is set up to analyze samples in various matrices, and (2) a daily calibration prior to use of the spectrometer for analyzing an unknown sample.

Figure 5:
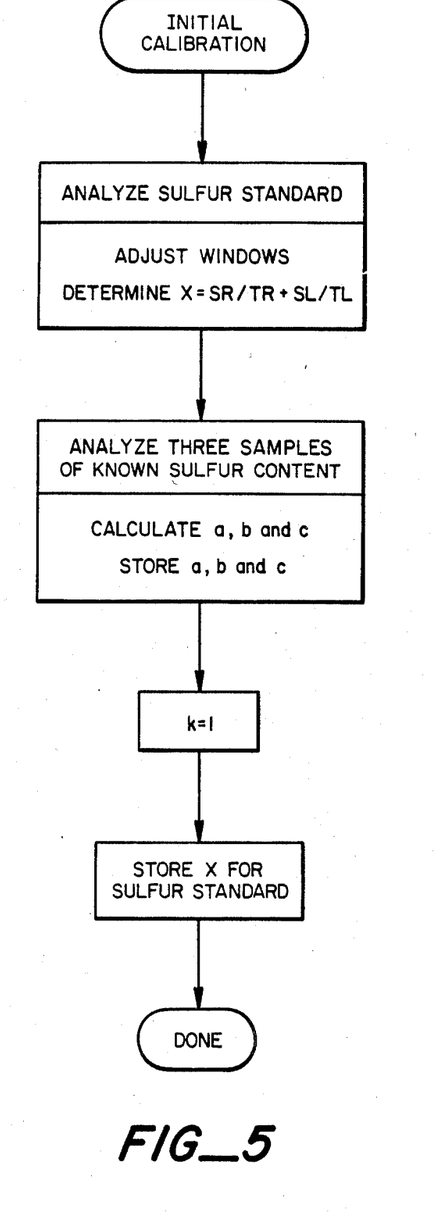
FIGS. 5 and 6, are flow charts of processes for effecting initial and daily calibration of the spectrometer of FIG. 1.

In the inital calibration, as illustrated in FIG. 5, the built-in standard is analyzed. For simplicity, a sulfur standard is used in this example. The windows which define TR and TL are adjusted until the ratio TR/TL is equal to a predetermined value, e.g., 1.00. The same is done for SR/SL, if the built-in standard contains sulfur or other elements, such as lead and molybdenum, which have fluorescence lines almost identical to the sulfur fluorescence line. With the windows thus moved to adjust for drift, the value of X is calculated for the built-in standard. However, if the built-in standard contains elements other than sulfur, and these elements have fluorescence lines at different energies than the sulfur fluorescence line, an additional step to establish the appropriate windows for sulfur is necessary. For example, in the case of a chlorine standard, the windows are first adjusted until EL/ER is equal to a predetermined value, e.g., 1.000, where EL and ER are areas under spectral curve on either side of the fluorescence peak of the element in the standard, which is chlorine in this case. The value of X' is calculated for the built-in standard, where $$X' = \frac{ER}{TR} + \frac{EL}{TL}.$$

The sulfur windows SR and SL are then established by moving the windows by an amount corresponding to the difference between the energy peaks for sulfur and the other element, e.g.

$SR = ER - 0.31$ (KeV)

$SL = EL - 0.31$ (KeV), where 0.31 KeV is the difference between the chlorine fluorescence line (2.62 KeV) and the sulfur fluorescence line (2.31 KeV). When the difference in the x-ray energies is small enough, the same electronic drift is applicable for both chlorine and sulfur lines. Therefore, the relationship SR/SL=1.000 is indirectly achieved. Three oil samples having known sulfur concentrations are then analyzed, and the values of X are determined for these samples. With the values of X and the known sulfur contents of the three samples, the constants a, b and c can be determined in the relationship $S = a(kX)^2 + b(kX) + c$, and these values are stored in the memory of the computer, together with the value X for the built-in sulfur standard or the value X' for the built-in non-sulfur standard. The constant k is set to a value of 1.000.

Figure 6:
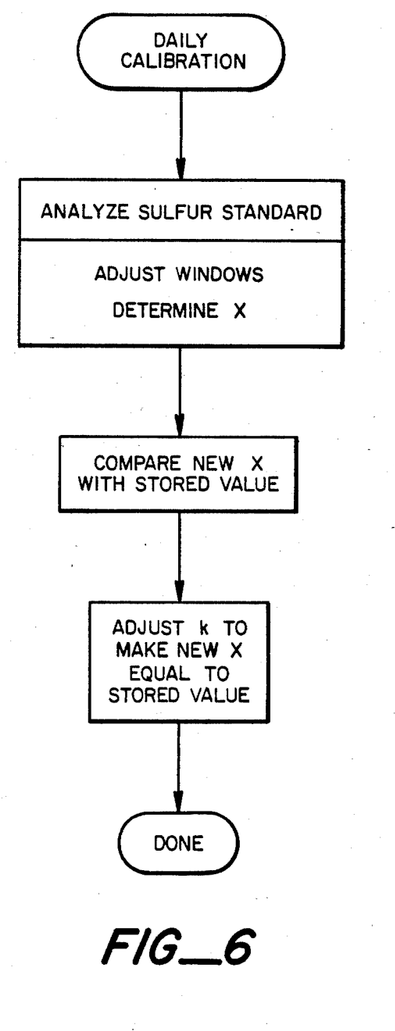

For daily calibration, as illustrated in FIG. 6, the built-in standard is once again analyzed, and the windows are adjusted to make TR/TL and SR/SL equal to their predetermined values, e.g., 1.00. The value of the constant k is then adjusted to make the newly determined X or X' value for the standard equal to the previously determined value, thereby compensating for variations in the x-ray tube voltage and any other changes in the instrument.

Figure 7:
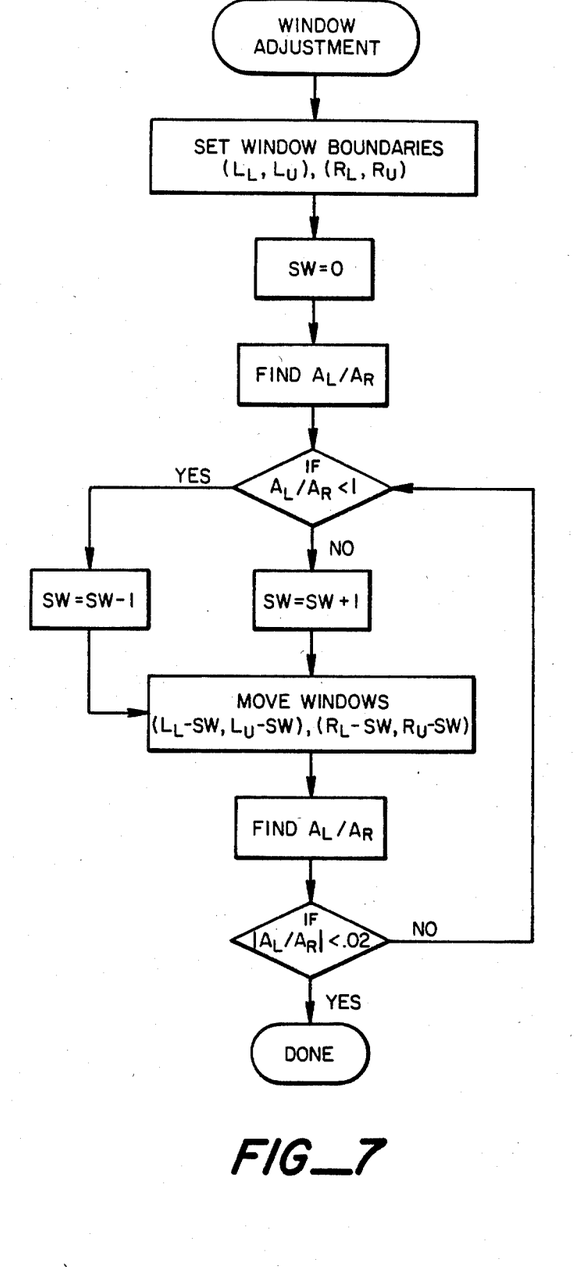
FIG. 7 is a flow chart of a subroutine for adjusting the sampling windows in the spectrometer of FIG. 1.

The manner in which the windows for the sulfur peak and the titanium peak are adjusted in one presently preferred embodiment is illustrated in FIG. 7. The windows for one peak are adjusted first, then the windows for the other peak are adjusted, using the same process for both adjustments. Initially, the boundaries for the windows are set to levels which are centered about the expected energy level of the photons to be detected. In FIG. 7, $L_L$ represents the lower boundary of the left window (i.e., SL or TL), $L_U$ represents the upper boundary of the left window, $R_L$ represents the lower boundary of the right window (i.e., SR or TR), and $R_U$ represents the upper boundary of the right window. An incremental counter SW is set to zero, and the ratio of the areas ($A_L/A_R$) under the sulfur or titanium peak is determined. If this ratio is less than 1, incremental counter SW is decremented, and if the ratio is equal to or greater than 1, the incremental counter is incremented. The windows are then shifted by subtracting the new value of SW from the numbers which define the boundaries of the windows. The ratio of the areas within the shifted windows is determined, and the adjustment process is repeated until the absolute value of this ratio is within a desired range, e.g. less than 0.02. In this example, each window is 32 increments wide, and each increment represents 20 eV.

In the event that the spectral curve should shift by more than the amount the windows can be moved, the biasing of the detector can be adjusted to bring the curve back to its proper position or to a position for which the windows can be adjusted.

If sulfur contents are to be determined in matrices which differ substantially from the matrix for which the system is calibrated, the values of the constants a, b and c determined for the first matrix are no longer applicable, but the calibration procedure can still be performed quickly and reliably. The initial calibration is performed with standards in each matrix to be analyzed, and the value X or X' of the built-in standard is determined on the basis of these standards. The system can store and recall many calibration curves, and therefore samples in widely differing matrices and having widely different sulfur contents can be analyzed with an appropriate calibration curve without recalibrating the system.

While the invention has been described with reference to the use of a specific quadratic relationship for calculating the sulfur content of a sample from the intensities of the sulfur line and the scattered target line, any polynomial expression which correctly relates the sulfur content to the spectral intensities can be employed. In general, the number of samples required for calibration of the spectrometer will be one greater than the order of the equation, e.g. three samples for a quadratic equation. Likewise, the constant k can be applied either to the individual terms, as above, or to the entire equation, e.g. $S=k(aX^2+bX+c)$. However, the value of the constant k may be calculated in different ways for different equations.

The invention has a number of important features and advantages. Any electronic drift is compensated by adjusting the window locations so that the shape of the calibration curve remains constant. Daily calibration can be done automatically and in a time of about five minutes, compared to 30–60 minutes for analyzers of the prior art. The use of the built-in standard is flexible, and users can select their own standards. The use of ratios makes the system independent of the intensity of the x-ray beam, and consequently stability of the x-ray tube intensity is not critical.

It is apparent from the foregoing that a new and improved spectrometer and method of calibrating the same have been provided. While only certain presently preferred embodiments have been described in detail, as will be apparent to those familiar with the art, certain changes and modifications can be made without departing from the scope of the invention as defined by the following claims.

We claim:

1. In a method of determining the sulfur content of a sample, the steps of: exciting the sample with x-rays of predetermined energy level to provide fluorescent energy corresponding to the elemental content of the sample and to the target line x-rays scattered by the sample, sampling the fluorescent energy in regions corresponding to the energy level of sulfur and to the energy level of the scattered target line x-rays, converting the sampled fluorescent energy to an electrical signal representative of the sulfur content of the sample, and calculating the sulfur content of the sample in accordance with a predetermined relationship.

2. The method of claim 1 including the steps of exciting a standard to provide a calibration signal, and adjusting the regions in which energy is sampled from the excited standard to maintain a consistent relationship between the sampled energy and the calibration signal.

3. In an x-ray fluorescence spectrometer for determining the sulfur content of a specimen: means for exciting the specimen with x-rays, means for providing an electrical signal corresponding to the energy spectrum of photons emitted by the excited specimen in predetermined regions corresponding to the energy levels of photons emitted by sulfur and target line x-rays scattered by the sample, and means responsive to the electrical signal for calculating the sulfur content of the sample according to the relationship $$S=a(kX)^2+b(kX)+c,$$

where S is the sulfur content, a, b, c and k are constants, $X=SR/TR+SL/TL$, SL and SR represent energy in two portions of the spectrum near the energy level of photons emitted by sulfur, and TL and TR represent energy in portions of the spectrum near the energy level of the scattered x-rays.

4. The spectrometer of claim 3 including means for adjusting the regions of the spectrum in which energy is analyzed to provide a calibration curve of predetermined shape.

5. The spectrometer of claim 3 including a standard which can be analyzed repeatedly in calibrating the system, and means for adjusting the value of the constant k to compensate for drift in the system between analyses of the standard.

6. In a method of calibrating an x-ray fluorescence spectrometer having a pulse height analyzer and a computer for analyzing the energy spectrum of photons emitted by a sample and determining the sulfur content of the sample in accordance with the relationship $$S=a(kX)^2+b(kX)+c,$$

where S is the sulfur content, a, b, c and k are constants, $X=ER/TR+EL/TL$, EL and ER represent energy in two portions of the spectrum near the energy level of photons emitted by a predetermined element, and TL and TR represent energy in portions of the spectrum near the energy level of scattered target line x-rays, the steps of: exciting a standard containing a reference element with x-rays and analyzing radiation from the sample in portions of the spectrum corresponding to the energy levels of photons emitted by the element in the standard and the target line x-rays scattered by the standard, adjusting the portions of the spectrum from which the radiation is analyzed to provide sampling windows which match the element and scattered target line x-ray peaks, finding and storing the value $X'=EL/TL+ER/TR$ of the standard, extrapolating the window adjustment to the sulfur windows, SR and SL, if sulfur is not the element in the standard, exciting three samples of known sulfur contents and analyzing the energy spectrum produced, establishing the constants a, b and c from the X values of the samples thereafter and prior to using the system to analyze a sample of unknown sulfur content, analyzing first the built-in standard, and readjusting the windows to correspond to the element and scattered target line x-ray peaks, determining the current $X'$ value of the standard and comparing the current to the stored value, calculating the constant k from the current $X'$ value and stored value, and utilizing the constant k in the relationship by which the sulfur content is determined to compensate for drift in the system.

7. The method of claim 6 wherein the computer is programmed to determine the sulfur content in accordance with the relationship $$S=a(kX)^2+b(kX)+c,$$

wherein S is the sulfur content, a, b, c and k are constants, $X=SR/TR+SL/TL$, SL and SR represent energy in two portions of the spectrum near the energy level of photons emitted by sulfur, and TL and TR represent energy to portions of the spectrum near the energy level of the scattered target line x-rays.

8. The method of claim 7 wherein the values of the constants a, b and c are determined by exciting and analyzing three samples of known sulfur content and calculating the values of said constants in accordance with the relationship $S=a(kX)^2+b(kX)+c$.

9. The method of claim 7 wherein the portions of the spectrum from which the radiation is analyzed are adjusted to make the ratios SR/SL and TR/TL each equal to a predetermined value.

10. The method of claim 7 wherein the constant k is adjusted to compensate for drift in the system.

11. In a method of calibrating an x-ray fluorescence spectrometer for determining the sulfur content of oil by exciting a sample of the oil with x-rays of predetermined energy level and analyzing the energy spectrum of photons emitted by the sample, the steps of: exciting a built-in standard containing a predetermined element with x-rays of the predetermined energy level, sampling the energy spectrum in two regions near the energy level of photons emitted by the element and providing electrical signals EL and ER corresponding thereto, sampling the energy spectrum in two regions near the energy level of target line x-rays scattered by the standard and providing electrical signals TL and TR corresponding thereto, adjusting the ratio of EL and ER and the ratio of TL and TR each to a predetermined value, determining and storing the value $X'=ER/TR+EL/TL$ for the built-in standard, extrapolating this window adjustment to the sulfur windows, SR and SL, if the element in the built-in standard is other than sulfur, exciting three samples of known sulfur content with x-rays of the predetermined energy level, sampling the energy spectrum to provide values of SL, SR, TL and TR for each of the three samples, calculating and storing the values of constants a, b and c in the relationship $$S=a(kX)^2+b(kX)+c,$$

where S is the percentage of sulfur in each of the three samples, k is a constant, and $X=SR/TR+SL/TL$ for each of the three samples, and setting the value of the constant k to a predetermined reference value.

12. The method of claim 11 including the steps of again exciting the built-in standard with x-rays of the predetermined energy level, adjusting the regions in which the energy spectrum is sampled to maintain the ratio of EL and ER and the ratio of TL and TR each at its predetermined value, adjusting the value of the constant k to make the value X' for the built-in standard the same as the value previously stored, and extrapolating this window adjustment to the sulfur windows, SR and SL, if the element in the built-in standard is other than sulfur.

13. In a method of calibrating an x-ray fluorescence spectrometer for determining the sulfur content of oil by exciting a sample of the oil with x-rays of predetermined energy level, analyzing the energy spectrum of photons emitted by the sample, and calculating the sulfur content according to the relationship $$S=k(aX^2+bX+c),$$

where S is the sulfur content of the sample, a, b, c and k are constants, $X=SR/TR+SL/TL$, SL and SR are spectral data representative of the energy present in first and second predetermined regions of the spectrum due to photons emitted by sulfur in the sample, and TL and TR are spectral data representative of the energy present in third and fourth predetermined regions of the spectrum due to the target line x-rays scattered by the sample, the steps of: exciting a standard with the x-rays, adjusting the predetermined regions of the energy spectrum to make the ratios SR/SL and TR/TL each equal to a predetermined value, exciting three samples of known sulfur content with the x-rays, calculating the values of constants a, b and c in the aforesaid relationship utilizing the known sulfur content and the spectral data for the three samples, calculating the apparent sulfur content of the standard utilizing the calculated values of the constants and the spectral data for the standard, storing the calculated apparent sulfur content of the standard for reference in final calibration of the system immediately prior to the use, once again exciting the standard with the x-rays to obtain new spectral data immediately prior to use of the system, adjusting the predetermined regions of the energy spectrum to maintain the ratios SR/SL and TR/TL each at its predetermined value, calculating the apparent sulfur content of the standard utilizing the previously calculated values of the constants a, b and c and the new spectral data, comparing the newly calculated apparent sulfur content of the standard with the previously stored apparent sulfur content, and adjusting the value of the constant k to make the newly calculated apparent sulfur content equal to the previously stored content.

14. In an x-ray fluorescence spectrometer for determining the sulfur content of a specimen: means for exciting the specimen to produce energy characteristic of the elemental content of the specimen, conversion means responsive to the energy for providing an electrical signal corresponding to the elemental content, a standard which is excited from time to time to provide energy and a calibration signal corresponding to the elemental content of the standard, said conversion means comprising means for sampling the energy in a region corresponding to the energy level characteristic of the element in the standard, and means for adjusting the region in which the energy is sampled to maintain a consistent relationship between the energy sampled and the calibration signal produced by excitation of the standard.

15. In an x-ray fluorescence spectrometer for determining the sulfur content of a specimen: means for exciting the specimen with x-rays having a predetermined energy level to produce fluorescent energy characteristic of the elemental content of the specimen, a standard which is excited from time to time to provide fluorescent energy and a calibration signal corresponding to the elemental content of the standard, conversion means responsive to the fluorescent energy for providing an electrical signal corresponding to the elemental content of the specimen or the sample producing the energy, said conversion means including means for sampling the fluorescent energy in a first region corresponding to the energy level characteristic of sulfur and in a second region corresponding to the energy level of x-rays scattered by the specimen, and means responsive to a combination of the energy sampled in the two regions for indicating the sulfur content of the specimen.

16. In an x-ray fluorescence spectrometer for determining the sulfur content of a specimen: means for exciting the specimen to produce fluorescent energy characteristic of the elemental content of the specimen, conversion means responsive to the fluorescent energy for providing an electrical signal corresponding to the elemental content, a standard containing an element having a characteristic x-ray fluorescence line falling between 1.0 and 4 KeV, said standard being excited from time to time to provide fluorescent energy and a calibration signal corresponding to the elemental content of the standard, and means for adjusting the conversion means to maintain a consistent relationship between the calibration signal and the fluorescent energy produced by the standard.

17. In an x-ray fluorescence spectrometer for determining the sulfur content of a specimen: means for exciting the specimen to produce fluorescent energy characteristic of the elemental content of the specimen, conversion means responsive to the fluorescent energy for providing an electrical signal corresponding to the elemental content, a sulfur standard which is excited from time to time to provide fluorescent energy and a calibration signal corresponding to the elemental content of the standard, and means for adjusting the conversion means to maintain a consistent relationship between the calibration signal and the fluorescent energy produced by the standard.

18. In an x-ray fluorescence spectrometer for determining the sulfur content of a specimen: means for exciting the specimen to produce fluorescent energy characteristic of the elemental content of the specimen, conversion means responsive to the fluorescent energy for providing an electrical signal corresponding to the elemental content, a standard which is excited from time to time to provide fluorescent energy and a calibration signal corresponding to the elemental content of the standard, said standard comprising a laminated body having two layers of film containing a predetermined element, the apparent overall content of the predetermined element in the standard being determined by the relative thicknesses of the two layers, and means for adjusting the conversion means to maintain a consistent relationship between the calibration signal and the fluorescent energy produced by the standard.

19. In a method for calibrating an x-ray fluorescence spectrometer for determining the sulfur content of a sample, the steps of: exciting a standard from time to time to provide fluorescent energy corresponding to the elemental content of the standard, converting the fluorescent energy to a calibration signal, sampling the fluorescent energy in a region corresponding to the energy level characteristic of the element in the standard, and adjusting the region to maintain a consistent relationship between the sampled energy and the calibration signal.

20. In a method for calibrating an x-ray fluorescence spectrometer for determining the sulfur content of a sample, the steps of: exciting a standard from time to time with x-rays having a predetermined energy level to provide fluorescent energy corresponding to the elemental content of the standard and the energy level of the x-rays, providing a calibration signal corresponding to the energy produced by the standard, sampling the fluorescent energy in a first region characteristic of the element and in a second region corresponding to the energy level of target line x-rays scattered by the standard, adjusting the regions to maintain a consistent relationship between the energy sampled and the calibration signal, and providing the calibration signal in accordance with a predetermined combination of the energies sampled in the two regions.

* * * * *